United States Patent
Mata et al.

(10) Patent No.: US 7,057,889 B2
(45) Date of Patent: Jun. 6, 2006

(54) APPARATUS AND METHOD FOR CABLE MANAGEMENT

(75) Inventors: Rizaldy Buencamino Mata, Milwaukee, WI (US); Thomas Verstegen, Mequon, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 157 days.

(21) Appl. No.: 10/065,970

(22) Filed: Dec. 5, 2002

(65) Prior Publication Data

US 2004/0114313 A1 Jun. 17, 2004

(51) Int. Cl.
*G06F 1/16* (2006.01)

(52) U.S. Cl. .................. 361/683; 242/85.1; 174/65 R; 315/362

(58) Field of Classification Search ........ 361/679–687, 361/736, 752, 826–827; 176/65–66; 128/660.01; 242/85.1; 174/65 R, 50; 439/501–502; 315/362

See application file for complete search history.

(56) References Cited

U.S. PATENT DOCUMENTS

| | | | | |
|---|---|---|---|---|
| 4,101,089 A | | 7/1978 | Culbertson et al. | 242/85.1 |
| 4,941,845 A | * | 7/1990 | Eppley et al. | 439/505 |
| 5,373,300 A | * | 12/1994 | Jenness et al. | 343/702 |
| 5,615,682 A | | 4/1997 | Stratz, Sr. | 128/662.03 |
| 5,804,765 A | | 9/1998 | Siemon et al. | 174/65 R |
| 6,163,465 A | | 12/2000 | Tanner et al. | 361/827 |
| 6,567,277 B1 | * | 5/2003 | Doherty et al. | 361/826 |
| 6,603,276 B1 | * | 8/2003 | Chansky et al. | 315/362 |
| 6,646,612 B1 | * | 11/2003 | Noguchi et al. | 343/702 |
| 2003/0181798 A1 | * | 9/2003 | Al-Ali | 600/324 |

* cited by examiner

*Primary Examiner*—Hung Van Duong
(74) *Attorney, Agent, or Firm*—Cantor Colburn LLP

(57) ABSTRACT

A monitoring device comprises a housing, a sensing device movable relative to the housing, and a cable having one end secured relative to the housing and another end secured to the sensing device. The housing includes a channel disposed therein and a portion of the cable is disposed in the channel for temporarily storing the cable. In one embodiment, a display screen is disposed in the housing, and the channel is disposed around at least a portion of a perimeter of the display screen. The cable may have a relaxed outside diameter greater than its stretched outside diameter, as in a coiled cable, thus allowing the cable to be stretched, inserted into the channel, and released to secure the cable in the channel. The cable may also be received in the channel in press-fit fashion.

5 Claims, 3 Drawing Sheets

APPARATUS AND METHOD FOR CABLE MANAGEMENT

BACKGROUND OF THE INVENTION

This invention relates to monitoring devices. More particularly, the invention relates to an apparatus and method for cable management in a monitoring device.

Monitoring devices, in general, include a display screen such as a cathode ray tube, liquid crystal display, or the like for displaying a graphical representation of a monitored condition. Monitoring devices also include a sensing device coupled to the monitoring devise by a cable. The sensing device is positioned relative to a body, a structure, etc. to sense the monitored condition.

One type of monitoring device is a patient monitoring device for medical use. Patient monitoring devices include, for example, blood pressure monitoring devices, electrocardiogram monitoring devices, ultrasound monitoring devices, and the like. In patient monitoring devices, the sensing device may include an ultrasound probe, a blood pressure cuff, electrical sensors, temperature sensors, sound sensors, an the like.

In monitoring devices, repeated storage and retrieval of the sensing device may cause the cables to become tangled, making it difficult and time consuming to take readings and troubleshoot the monitoring device. When the cables become tangled, the cables may need to be unplugged to facilitate untangling, resulting in a temporary loss of monitoring. Also, when a monitoring device is being transported or stored, the cables drape from the monitoring device. This can lead to the cables becoming tangled and can make transport or storage difficult.

BRIEF SUMMARY OF THE INVENTION

The above-described drawbacks and deficiencies are overcome or alleviated by a monitoring device comprising a housing, a sensing device movable relative to the housing, and a cable having one end secured relative to the housing and another end secured to the sensing device. The housing includes a channel disposed therein and a portion of the cable is removably disposed in the channel for temporary storage of the cable. In one embodiment, a display screen is disposed in the housing, and the channel is disposed around at least a portion of a perimeter of the display screen.

In another aspect, a method of storing a cable in a monitoring device comprises: extending the cable to reduce an outside diameter of the cable to less than that of a channel formed in the monitoring device; disposing the cable in the channel; and releasing the extended cable to secure the cable within the channel.

The above discussed and other features and advantages of the present invention will be appreciated and understood by those skilled in the art from the following detailed description and drawings.

BRIEF DESCRIPTION OF THE DRAWINGS

Referring to the exemplary drawings wherein like elements are numbered alike in the several Figures.

DETAILED DESCRIPTION OF THE INVENTION

Figure 1:
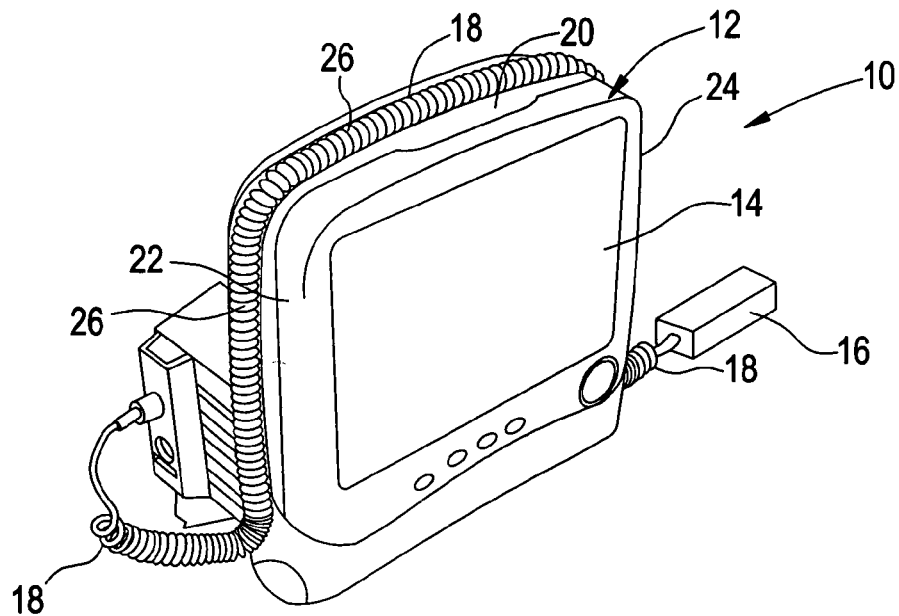
FIG. 1 is a front perspective view of a monitoring device including a channel disposed therein for storing a cable.
Figure 2:
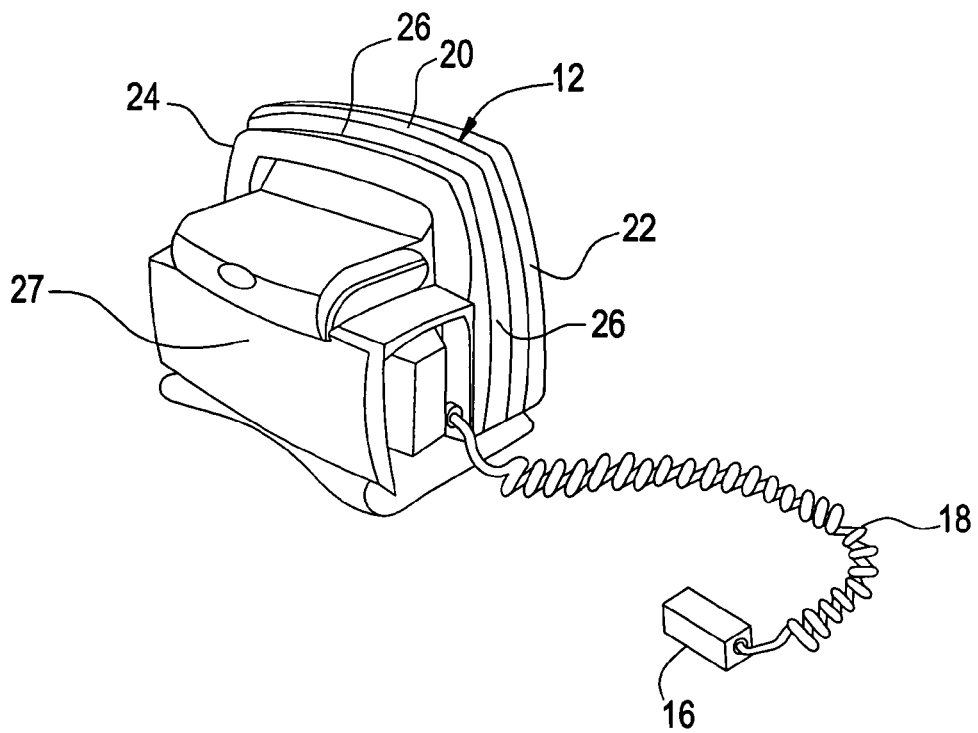
FIG. 2 is a rear perspective view of the monitoring device of FIG. 1 with the cable removed from the channel.

Referring to FIGS. 1 and 2 a perspective view of a monitoring device 10 is shown. Monitoring device 10 may include, for example, a patient monitoring device, such as a blood pressure monitoring device, an electrocardiogram monitoring device, an ultrasound monitoring device, or the like. Monitoring device 10 includes a housing 12 for mounting display screen 14 such as a cathode ray tube, liquid crystal display, or the like for displaying a graphical representation of a monitored condition. A sensing device 16 is coupled to the monitoring device 10 by a cable 18. A portion of the cable 18 external to the housing 12 is movable relative to the housing 12, allowing the sensing device 16 to be manipulated. A human operator, such as a physician or technician, manipulates the sensing device 16 relative to a target object to sense the monitored condition. Such sensing devices 16 may include, for example, an ultrasound probe, a blood pressure cuff, electrical sensors, temperature sensors, and sound sensors. One end of the cable 16 is secured the housing 12 of the monitoring device 10. In the example shown, the cable 18 is secured to the same housing 12 as the display screen 14. It will be appreciated, however, that cable 18 may be secured to a point on the monitoring device 10 separate from the housing 12 containing the display screen 14.

The housing 12 of the monitoring device 10 includes a top wall 20, a first side wall 22 adjacent the top wall 20, and a second side wall 24 adjacent the top wall 20. The display screen 14 extends between the top wall 20 and the first and second side walls 22 and 24. A channel 26 is formed in the housing 12 around a portion of the perimeter of the display screen 14. The channel 26 extends along the first side wall 22, along top wall 20, and along the second side wall 24. In the embodiment shown, channel 26 is contiguous between the side walls 22 and 24 and the top wall 20. Channel 26 may, however, be formed in any one or more of first or second side walls 22 and 24, top wall 20, or a back wall 27 of housing 12, and may extend in a route across any one or more of these walls different from that shown.

Figure 3:
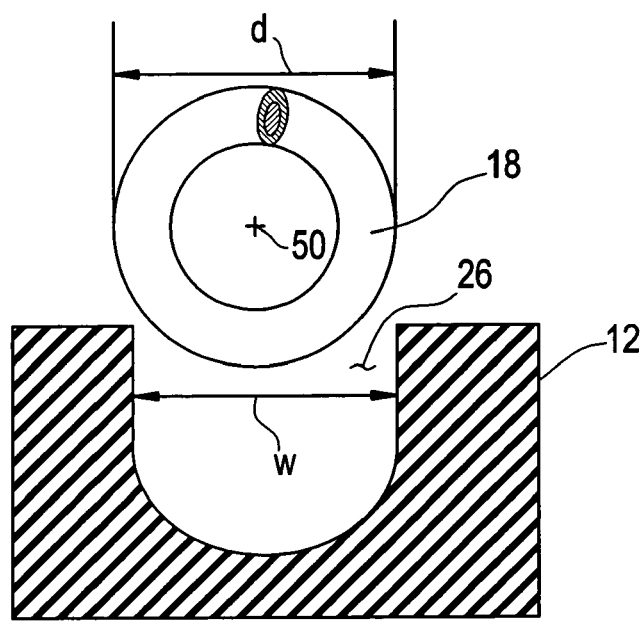
FIG. 3, is a cross sectional view of the cable and the channel for storing the cable.

Referring to FIG. 3, a cross sectional view of cable 18 and channel 26 is shown. In the embodiment of FIGS. 1–3, cable 18 is coiled to form a spring. When cable 18 is relaxed, i.e., when no external force is applied to stretch cable 18, the cable 18 has a first overall length, i.e., a length measured along an axis 50 of the spiral from the point of attachment to the monitoring device 10 to the point of attachment to the sensing device 16, and an outside diameter, which is indicated at d. As shown in FIG. 3, when the cable 18 is relaxed, the diameter d is greater than the width w of the channel 26. When cable 18 is stretched to an overall length greater than the first overall length, the outside diameter d can be reduced to less than the width w of the channel 26, thus allowing cable 18 to be placed in channel 26. When cable 18 is inserted in channel 26 and the external stretching force on the cable 18 is released, the outside diameter d of the cable 18 expands to contact the sides of the channel 26, thus securing cable 18 within channel 26. Accordingly, a user of the monitoring device 10 can store the cable 18 by: extending the cable 18 to reduce the outside diameter d to less than the width w of the channel 26; disposing the cable 18 into the channel 26; and releasing the extended cable 18 to secure the cable 18 within the channel 26.

Figure 4:
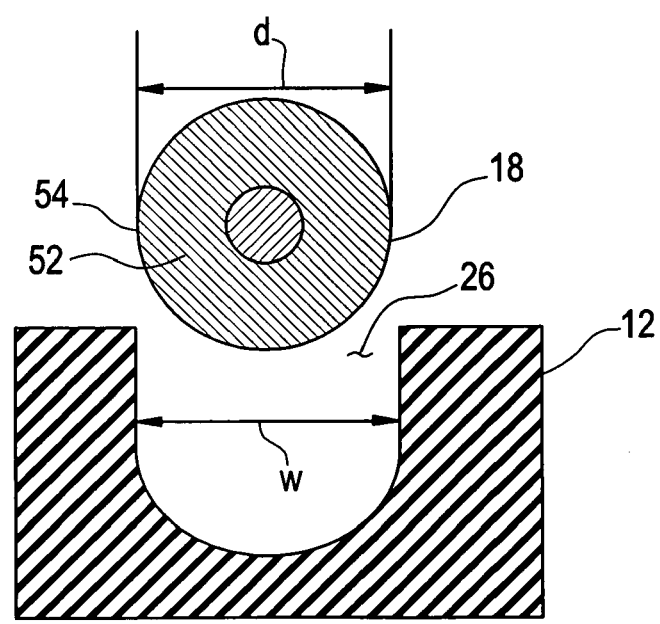
FIG. 4, is a cross sectional view of an alternative embodiment of the cable and the channel for storing the cable.

FIG. 4 is an alternative embodiment of the channel 18 and cable 26, wherein the portion of cable 18 extending from the housing 12 is received in the channel 26 in press-fit fashion. Referring to FIG. 4, cable 18 is straight, rather than spiraled, and includes a resilient material 52 forming an outer surface 54 thereon. The outside diameter d of the cable 18 is dimensioned relative to the width w of the channel 26 to create a press-fit with the sides of the channel 26. That is, when the cable 18 is disposed in the channel 26, the outer surface 54 contacts the sides of the channel 26 such that the resilient material 52 is compressed. As a result of this press-fit, the cable 18 is secured within the channel 26.

Figure 5:
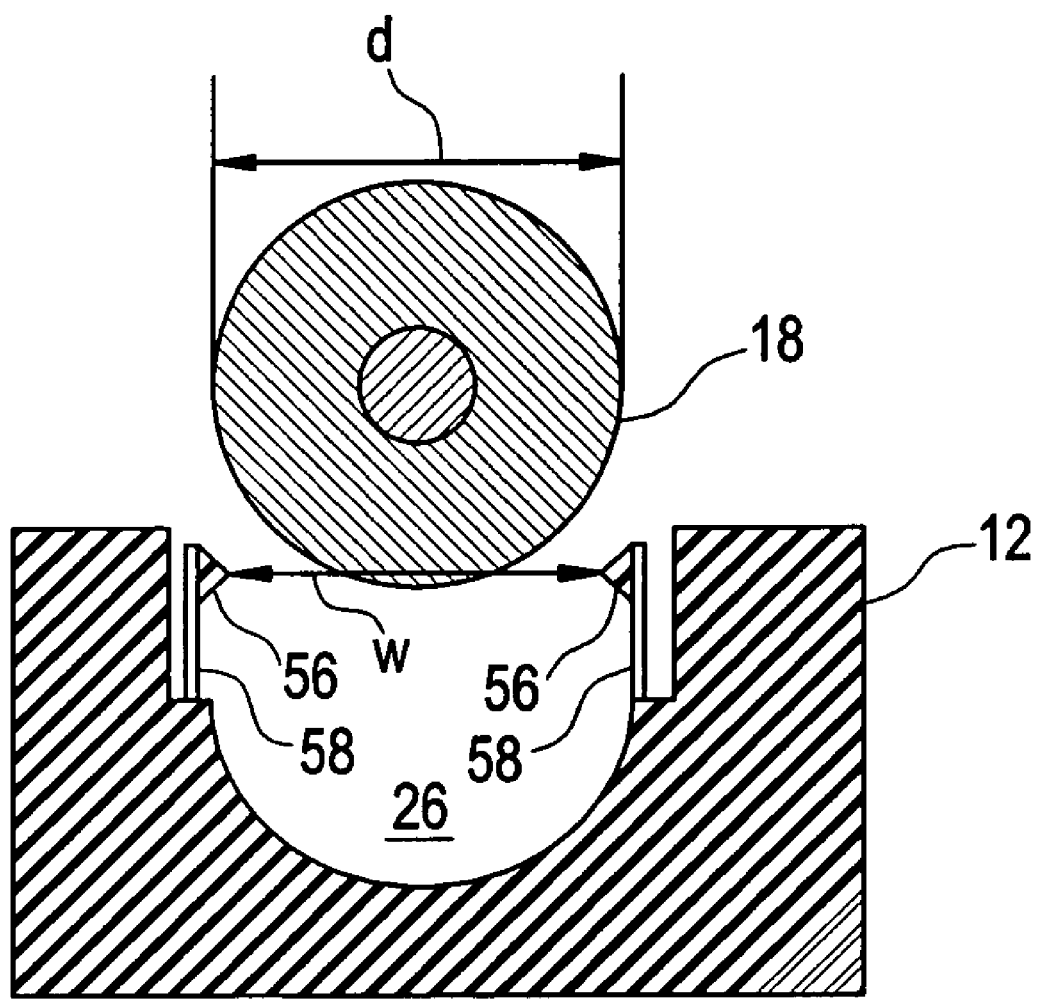
FIG. 5, is a cross sectional view of another alternative embodiment the cable and the channel for storing the cable.

FIG. 5 is another alternative embodiment of the channel 26 and cable 18, wherein the portion of cable 18 extending from the housing 12 is received in the channel 26 in press-fit fashion. Referring to FIG. 5, cable 18 is straight, rather than spiraled, and channel 26 includes one or more detents 56 formed on one or more sides of the channel 26. The width w between the detents 56 is less than the diameter d of the cable 18. In the embodiment shown, detents 56 are mounted on resilient arms 58. Insertion of cable 18 into the channel 26 spreads resilient arms 58 to allow cable 18 to pass between detents 56. When cable 18 is fully inserted, detents 56 secure cable 18 within channel 26. Alternatively, detents 56 may be fixed to the sides of the channel 26 without resilient arms 58, and a resilient cover may be used on cable 18 as in the embodiment of FIG. 4. In this embodiment, detents 56 deflect the resilient cover 18 of the cable 18 as the cable 18 is inserted into the channel 26, and, when the cable 18 is fully inserted 56, detents secure cable 18 within channel 26.

In any of the embodiments described hereinabove, the cable 18 may be removed from the channel 26 by pulling the cable 18 away from the channel 26. With the cable 18 removed from the channel 26, as shown in FIG. 2, the sensing device 16 can be manipulated by an operator to sense the monitored condition.

With the apparatus and method for cable management described herein, the cable can be repeatedly stored and retrieved without becoming tangled. As a result, the apparatus and method make it less difficult and time consuming to take readings and to troubleshoot the monitoring device, and reduce the need to unplug the cables to facilitate untangling. Also, with this apparatus and method, transportation and storage of the monitoring device can be performed without the problems associated with dangling cables.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A monitoring device comprising:
    a sensing device;
    a cable secured to the sensing device;
    a display screen;
    a housing for the display screen, the housing including;
    a topwall;
    a first side wall adjacent the top wall;
    a second side wall adjacent the top wall, the display screen extending between the top wall, the first side wall, and the second side wall;
    a first channel formed in at least one of the top wall, the first side wall, and the second side wall, the cable being removably received in the channel; and
    a second channel disposed in the second side wall, the cable being removably disposed in the second channel.

2. The monitoring device of claim 1, further comprising:
    a third channel disposed in the top wall, the cable being removably disposed in the third channel.

3. The monitoring device of claim 2 wherein the first, second, and third channels are contiguous.

4. The monitoring device of claim 3, wherein the cable has a relaxed outside diameter and a stretched outside diameter, the relaxed outside diameter being greater than a width of the channel and the stretched outside diameter being less than the width of the channel.

5. The monitoring device of claim 3, wherein the cable is received in the channel in press-fit fashion.

* * * * *

UNITED STATES PATENT AND TRADEMARK OFFICE
CERTIFICATE OF CORRECTION

PATENT NO. : 7,057,889 B2 Page 1 of 1
APPLICATION NO. : 10/065970
DATED : June 6, 2006
INVENTOR(S) : Mata et al.

It is certified that error appears in the above-identified patent and that said Letters Patent is hereby corrected as shown below:

Column 1,
Line 23, before "the", delete "an" and insert therefor --and--.
Line 66, after "FIG.", delete "3," and insert therefor --3--.

Column 2,
Line 1, after "FIG.", delete "4," and insert therefor --4--.
Line 3, after "FIG.", delete "5," and insert therefor --5--.
Line 26, after "cable", delete "16" and insert therefor --18--.
Line 27, before "the" (first instance) , insert --to--.

Column 3,
Line 30, after "cover", delete "18".
Line 32, after "fully", delete "inserted 56, detents" and insert therefor --inserted, detents 56--.

Signed and Sealed this

Sixth Day of March, 2007

JON W. DUDAS
*Director of the United States Patent and Trademark Office*